US008812067B2

(12) United States Patent  (10) Patent No.: US 8,812,067 B2
Leigh et al.  (45) Date of Patent: Aug. 19, 2014

(54) MULTI ORIENTATION CRYOSTATS

(75) Inventors: Benjamin David Leigh, Ifield (GB); Masayuki Nakatsu, Pulborough (GB)

(73) Assignee: Tesla Engineering Limited, Suzzex (GB)

( * ) Notice: Subject to any disclaimer, the term of this patent is extended or adjusted under 35 U.S.C. 154(b) by 162 days.

(21) Appl. No.: 13/428,236

(22) Filed: Mar. 23, 2012

(65) Prior Publication Data

US 2013/0237425 A1  Sep. 12, 2013

(30) Foreign Application Priority Data

Mar. 6, 2012 (EP) .................................. 12158274

(51) Int. Cl.
*H01F 6/06*  (2006.01)
(52) U.S. Cl.
USPC .......................................................... 505/163
(58) Field of Classification Search
USPC ................................ 505/163; 335/216; 62/51
See application file for complete search history.

(56) References Cited

U.S. PATENT DOCUMENTS

| 4,507,616 | A | | 3/1985 | Blosser et al. |
| 4,633,125 | A | * | 12/1986 | Blosser et al. .................. 313/62 |
| 4,641,057 | A | | 2/1987 | Blosser et al. |
| 7,696,847 | B2 | * | 4/2010 | Antaya ......................... 335/216 |

* cited by examiner

*Primary Examiner* — Colleen Dunn
(74) *Attorney, Agent, or Firm* — Jeffrey K. Riddle; Van Cott, Bagley, Cornwall & McCarthy P.C.

(57) ABSTRACT

A multi-orientation cryostat 5 for a superconducting magnet 4 for use in a plurality of orientations. The cryostat 5 comprises a vessel 6 for holding cryogenic liquid and, leading away from the vessel, a quench duct 7 for allowing escape from the vessel of gas generated by boiling of the cryogenic liquid due to quenching of the magnet. The quench duct 7 is sinuous so as to provide at least to differently orientated anti-convection portions 71, each portion for functioning as an anti-convection portion with the cryostat in a respective corresponding orientation.

22 Claims, 6 Drawing Sheets

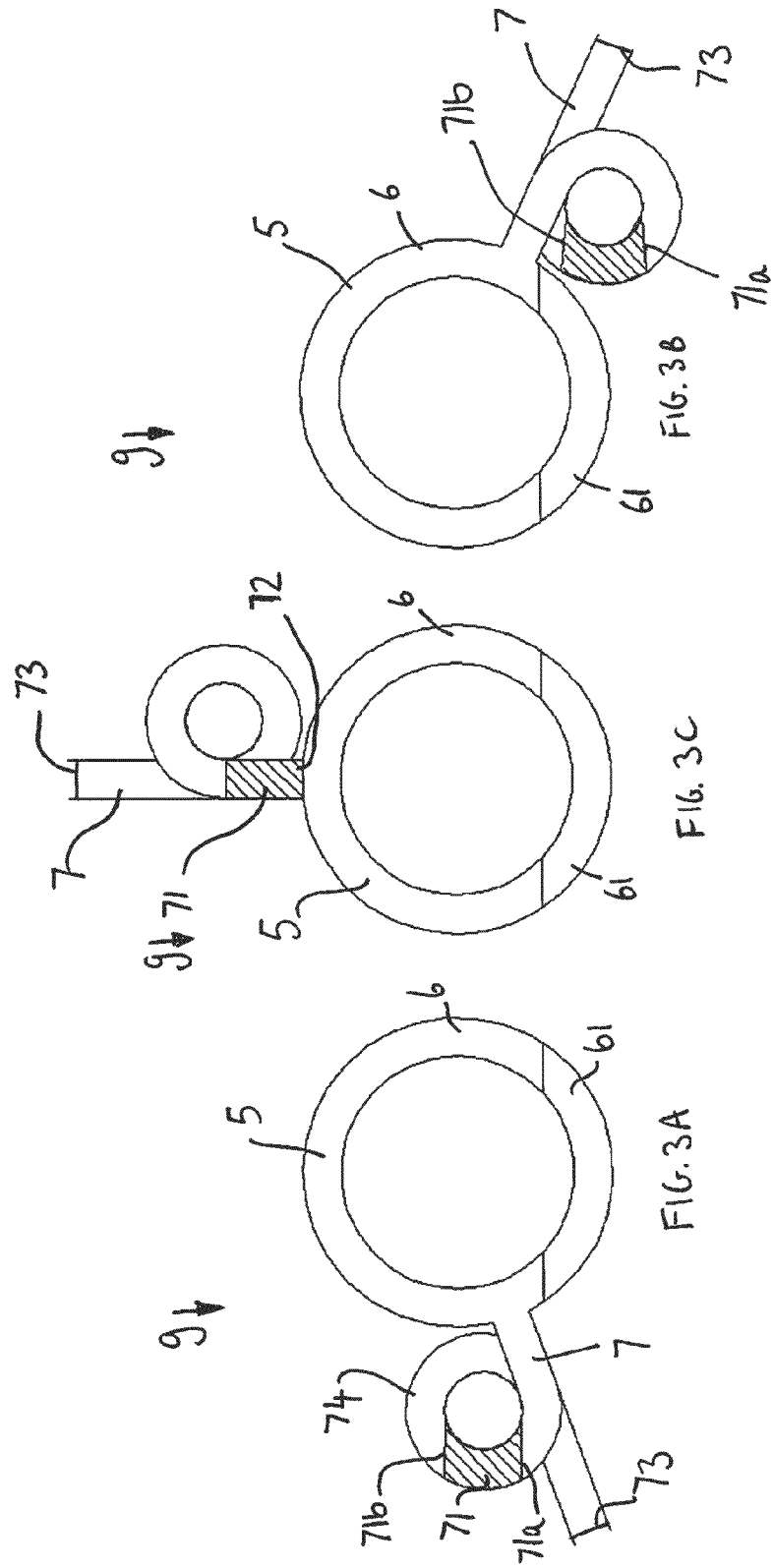

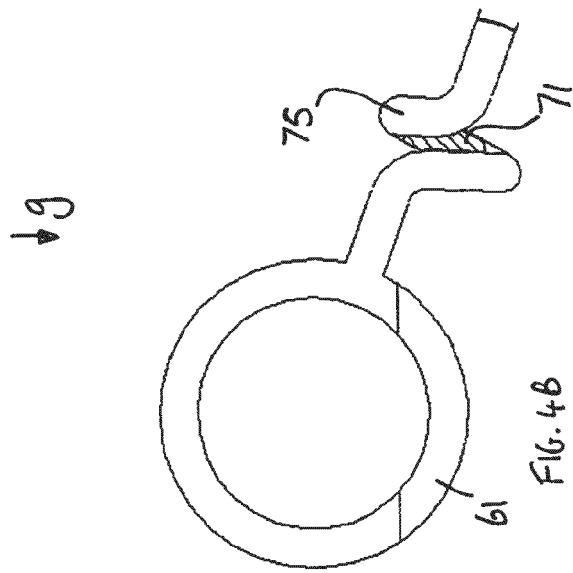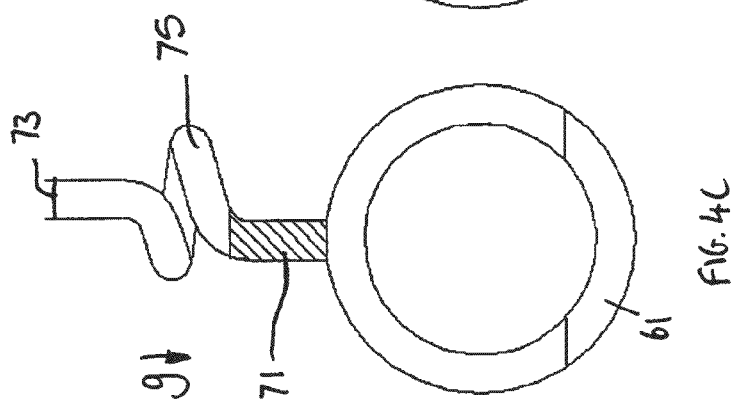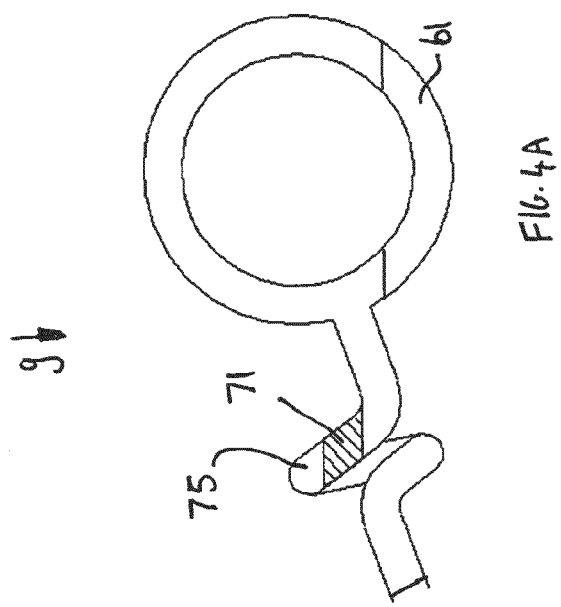

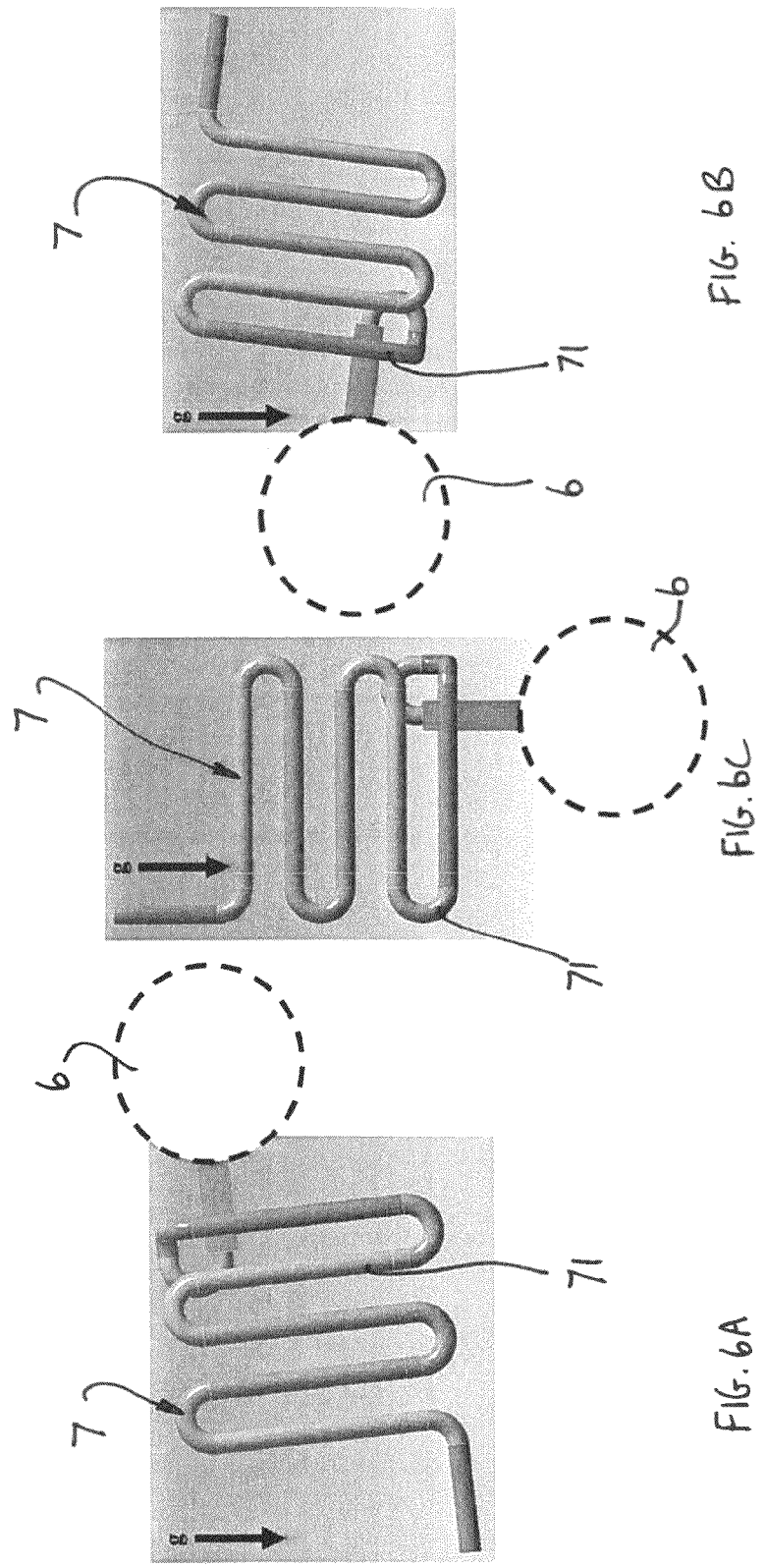

MULTI ORIENTATION CRYOSTATS

The present application claims the benefit under 35 U.S.C. §119(a)-(d) of European Patent Application No. EP 12158274 filed Mar. 6, 2012. This application is herein incorporated by reference in its entirety.

This invention relates to multi orientation cryostats, and superconducting magnet arrangements including such cryostats, as well as medical equipment apparatus including such cryostats.

Superconducting magnets are generally required to be maintained at a "low temperature" in order to maintain their superconducting properties. Cryostats are provided for maintaining superconducting magnets at superconducting temperatures.

A cryostat comprises a vessel for holding a cryogenic liquid to act as a coolant. Refrigeration systems will be provided to cool the carried cryogenic liquid and/or cool replacement liquid for feeding to the cryostat.

Superconducting magnets are typically at risk of quenching. Superconducting magnets typically embody very large stored energy in their magnetic fields (e.g. 1 MJ and upwards). However due to the very low heat capacity of materials close to absolute zero a tiny energy disturbance (1 mJ or less) may drive part of the coil above its local superconducting transition temperature into the normal resistive state. If the disturbance exceeds a stability threshold it will propagate through the windings until some or all of them become resistive. Inevitably the stored magnetic energy is then rapidly converted to heat in the resistive windings. The heat leads to rapid boil off of the cryogenic liquid, which is converted to gas, and expands significantly as it warms (for example 700:1 for liquid helium at 4.2K expanding to become gas at room temperature and atmospheric pressure).

This undesirable and abnormal termination of the magnet's superconducting operation, as the coil or part of the coil returns to the normal resistive state, is known as a quench.

Quenching is expensive and undesirable. The risk of quenching can be minimised by good design and good practice but nevertheless superconducting magnets must be designed to survive quenching, including avoiding over pressure of the vessel of the cryostat carrying the cryogenic cooling liquid.

This is achieved by the provision of a quench duct which provides a path by which rapidly expanding and warming cryogenic fluid, and more particularly cryogenic gas, can escape the vessel.

Quench ducts need to be relatively wide bored to allow the expanding gas produced by a quench to safely escape the cryostat vessel.

On the other hand, a fill tube or normal vent tube which is provided in a cryostat for normal operation of the magnet will generally be of much smaller cross sectional area. This is because there is not the need to provide such a tube with a large bore and a large bore is generally undesirable as it will tend to increase heat leakage into the cryostat. Thus, in a superconducting magnet arrangement there will be typically a quench duct which is distinct from any fill tube. Further the quench duct will be distinct from any vent tube, or at the very least there will be a different outlet end for any present vent tube than the quench duct. To put this another way, a quench duct is identifiably different from a fill tube or a normal vent tube.

Because the quench duct needs to be of a relatively wide bore it can generate a problem in terms of it being a heat leakage path into the cryostat and can cause undesirable warming of the cryogenic liquid.

In normal circumstances this potential problem is mitigated against by ensuring that the quench duct extends vertically or near vertically away from the cryostat vessel during operation of the magnet. This creates a temperature inversion in the quench duct which suppresses convection. Thus a conventional quench duct has an anti-convection portion which will function when correctly orientated and in use, by virtue of the temperature inversion. This is important because otherwise convection currents will tend to transfer heat into the cryostat.

This arrangement can function well in a normal superconducting magnet arrangement.

However there are circumstances where it is required to use a superconducting magnet arrangement, and hence cryostat, in different orientations. Typically, in such cases the superconducting magnet arrangement will be mounted in such a way that it is movable relative to a base of the equipment in which it is installed such that the orientation of the superconducting magnet, and hence cryostat, changes as the superconducting magnet arrangement is moved. The equipment may be medical equipment apparatus. One example of such a machine is a gantry mounted cyclotron used to provide proton therapy treatment. In such an apparatus the cyclotron (including the superconducting magnet arrangement) moves in an approximately 180 degree arc around a patient and correspondingly the orientation of the superconducting magnet arrangement and cryostat changes through 180 degrees between one end of this arc and the other. This means, for example, that if the quench duct is orientated vertically or near vertically in the midpoint of this arc it will be orientated horizontally or near horizontally at both end positions of the arc.

When the quench duct is no longer in a vertical or near vertical orientation a convection cell can set up since the temperature inversion (relative to gravity) no longer exists. Thus heat can tend to be pumped from the warm end of the quench duct (i.e. the outlet end) and the cold end (i.e. the inlet end). Such a situation is illustrated in FIG. 2 which is described in more detail further below. When this arises it can cause an undesirable heat leakage into the cryostat which may risk causing excessive boil off of the cryogenic liquid which in turn could potentially lead to a quench. Alternatively or in addition where a quench duct may be moved away from the vertical this may lead to increased costs in terms of providing more refrigeration for the cryogenic liquid and/or a more complicated and higher rated refrigeration system.

The present invention is aimed at addressing at least some of these issues.

According to a first aspect of the present invention there is provided a multi-orientation cryostat for a superconducting magnet for use in a plurality of orientations, the cryostat comprising a vessel for holding cryogenic liquid and, leading away from the vessel, a quench duct for allowing escape from the vessel of gas generated by boiling of the cryogenic liquid due to quenching of the magnet, wherein the quench duct is sinuous so as to provide at least two differently orientated anti-convection portions, each portion for functioning as an anti-convection portion with the cryostat in a respective corresponding orientation.

This arrangement allows the provision of a quench duct which can operate effectively with the cryostat in multiple orientations whilst providing good insulation performance to minimise the cooling requirement for the carried cryogenic liquid.

A burst disc may be provided at or towards an end of the quench duct remote from the vessel.

The quench duct may be distinct from any fill tube and may be distinct from any vent tube or at least the quench duct may have a separate outlet to the vent tube outlet. Vent and fill tubes will typically have a smaller cross section than the quench duct since vent and fill tubes are not required to handle the large volume of quickly expanding gas which will be produced during quenching of the cooled magnet.

The quench duct may be tube like. Each anti-convection portion may be a tube like portion of the tube like quench duct.

The quench duct may comprise a plurality of anti-convection portions. The quench duct may comprise more than two anti-convection portions.

The orientation of at least one of the anti-convection portions may be separated by at least 90 degrees from the orientation of at least another one of the anti-convection portions. There may be at least three anti-convection portions in sequence along the flow path through the quench duct within the orientation of a first of the anti-convection portions separated by at least 90 degrees from the orientation of a second of the anti-convection portions and the orientation of a third of the anti-convection portions separated by at least 90 degrees from the orientation of the second of the anti-convection portions. Each of the anti-convection portions may run in the same plane as the other anti-convection portions or in parallel planes.

The plane or parallel planes may have the axis of rotation as a normal.

The quench duct may have an inlet portion which is arranged to remain above the level of the carried cryogenic liquid in normal operation.

The multi-orientation cryostat may be arranged for use in a first orientation and a second orientation reachable from the first orientation by a rotational transformation, and may be arranged for use in orientations between the first orientation and the second orientation reachable by execution of part of said rotational transformation from the first orientation. A first portion of the quench duct may act as an anti-convection portion when the cryostat is in the first orientation and a second portion of the quench duct may act as an anti-convection portion when the cryostat is in the second orientation.

There may be at least 90 degrees, and preferably at least 135 degrees and more preferably still at least 180 degrees, of rotation between the first orientation and the second orientation.

The quench duct may have three anti-convection portions with a first portion of the quench duct acting as an anti-convection portion when the cryostat is in the first orientation, a second portion of the quench duct acting as an anti-convection portion when the cryostat is in the second orientation, and a third portion of the quench duct acting as an anti-convection portion when the cryostat is in an orientation between the first orientation and the second orientation.

The quench duct may include a continuous bend portion, such as a u-bend portion, or a loop portion, or a spiral bend portion, the continuous bend portion may turn through at least 90 degrees, preferable in the order of at least 180 degrees and possibly 360 degrees. Selected parts of the continuous bend portion may act as anti-convection portions when the cryostat is in corresponding selected orientations.

When in an operative position, each anti-convection portion will extend upwardly having a lower end and an upper end with the lower end closer, in terms of a flow path through the quench duct from the vessel, to the vessel than the upper end.

The quench duct may be arranged such that when the multi-orientation cryostat is in any one of the first orientation, the second orientation and the orientations between the first orientation and the second orientation, the quench duct provides a tube portion extending upwardly having a lower end and an upper end with the lower end closer, in terms of a flow path through the quench duct from the vessel, to the vessel than the upper end, to act as an anti-convection portion.

The inlet portion of the quench duct may be arranged to remain above the level of the carried cryogenic liquid when the multi-orientation cryostat is in any one of the first orientation, the second orientation and the orientations between the first orientation and the second orientation.

The cryostat may comprise a single quench duct.

The multi-orientation cryostat may be a rotatable cryostat.

According to a second aspect of the present invention there is provided a superconducting magnet arrangement comprising a superconducting magnet and multi-orientation cryostat as defined above.

According to a third aspect of the present invention there is provided medical equipment apparatus comprising a superconducting magnet arrangement as defined above mounted for movement relative to a base of the medical equipment apparatus between a first position where the cryostat is in said first orientation and a second position where the cryostat is in said second orientation.

According to a fourth aspect of the present invention there is provided medical equipment apparatus comprising a superconducting magnet arrangement mounted for movement relative to a base of the medical equipment apparatus between a first position and a second position, the superconducting magnet arrangement comprising a superconducting magnet and a cryostat comprising a vessel for holding cryogenic liquid and leading away from the vessel, a quench duct for allowing escape from the vessel of gas generated by boiling of the cryogenic liquid due to quenching of the magnet, wherein the cryostat is in a first orientation when the magnet arrangement is in the first position and the cryostat is in a second orientation when the magnet arrangement is in the second position and wherein, the quench duct is sinuous so as to provide at least a first anti-convection portion and a second anti-convection portion which are differently orientated from one another, with the first anti-convection portion functioning in use as an anti-convection portion with the cryostat in the first orientation and the second anti-convection portion functioning in use as an anti-convection portion with the cryostat in the second orientation.

The quench duct may comprise a plurality of anti-convection portions each for functioning as an anti-convection portion when the cryostat is in a respective corresponding orientation.

According to a fifth aspect of the present invention there is provided medical equipment apparatus comprising a superconducting magnet arrangement mounted for movement relative to a base of the medical equipment apparatus between a first position and a second position, the superconducting magnet arrangement comprising a superconducting magnet and a cryostat comprising a vessel for holding cryogenic liquid and, leading away from the vessel, a quench duct for allowing escape from the vessel of gas generated by boiling of the cryogenic liquid due to quenching of the magnet, wherein the cryostat is in a first orientation when the magnet arrangement is in the first position and the cryostat is in a second orientation when the magnet arrangement is in the second position and wherein, the quench duct is sinuous so as to provide at least a first portion and a second portion which are differently orientated from one another in such a way that:

when the cryostat is in the first orientation, the first portion extends upwardly relative to the base of the equipment and has a lower end and an upper end with the lower end closer, in terms of a flow path through the quench duct from the vessel, to the vessel than the upper end; and when the cryostat is in the second orientation, the second portion extends upwardly relative to the base of the equipment and has a lower end and an upper end with the lower end closer, in terms of a flow path through the quench duct from the vessel, to the vessel than the upper end.

This facilitates a temperature inversion in the first portion in the first orientation and in the second portion in the second orientation to help prevent convection currents that would tend to cause heat leakage along the quench duct towards the vessel.

According to a sixth aspect of the present invention there is provided a multi-orientation cryostat for a superconducting magnet, the cryostat comprising a vessel for holding cryogenic liquid and, leading away from the vessel, a quench duct for allowing escape from the vessel of gas generated by boiling of the cryogenic liquid due to quenching of the magnet, wherein the quench duct is sinuous so as to provide at least two differently orientated portions.

The quench duct may be tube like. Each differently orientated portion may be a tube like portion of the tube like quench duct.

The quench duct may comprise a plurality of differently orientated portions. The quench duct may comprise more than two differently orientated portions.

The orientation of at least one of the quench duct portions may be separated by at least 90 degrees from the orientation of at least another one of the quench duct portions.

The quench duct may include a continuous bend portion, such as a u-bend portion, or a loop portion, or a spiral bend portion, the continuous bend portion may turn through at least 90 degrees, preferable in the order of at least 180 degrees.

The quench duct may have a first portion and a second portion which are differently orientated from one another in such a way that the cryostat may be placed in a first orientation and a second orientation reachable from the first orientation by a rotational transformation of at least 90 degrees and where the first and second orientations are such that:

when the cryostat is in the first orientation, the first portion extends upwardly and has a lower end and an upper end with the lower end closer, in terms of a flow path through the quench duct from the vessel, to the vessel than the upper end; and when the cryostat is in the second orientation, the second portion extends upwardly and has a lower end and an upper end with the lower end closer, in terms of a flow path through the quench duct from the vessel, to the vessel than the upper end.

Preferably a rotational transformation of at least 135 degrees, more preferably at least 180 degrees, is required to reach the second orientation from the first orientation.

According to another aspect of the invention there is provided a method of operating a cryostat, magnet or medical equipment apparatus defined above comprising filling the vessel with cryogenic liquid and moving the cryostat between a first and a second orientation.

The optional features defined above following each aspect of the invention are not all repeated following each other aspect of the invention in the interests of brevity. However, it should be understood that any optional features of any of the aspects of the invention mentioned above may also be optional features of any other of the aspects with changes in wording as necessary.

Embodiments of the present invention will now be described, by way of example only, with reference to the accompanying Figures in which:

FIG. 1 schematically shows medical equipment apparatus including a superconducting magnet arrangement having a rotatable cryostat;

FIGS. 3A to 3C show a first rotatable cryostat embodying the invention which may be used in the apparatus shown in FIG. 1, with the cryostat shown in a first orientation in FIG. 3A, a second orientation in FIG. 3B, and an intermediate orientation in FIG. 3C.

FIGS. 4A to 4C show a second rotatable cryostat embodying the invention which may be used in the apparatus shown in FIG. 1, with the cryostat shown in a first orientation in FIG. 4A, a second orientation in FIG. 4B, and an intermediate orientation in FIG. 4C.

FIGS. 6A to 6C show a fourth rotatable cryostat embodying the invention which may be used in the apparatus shown in FIG. 1, with the cryostat shown in a first orientation in FIG. 6A, a second orientation in FIG. 6B, and an intermediate orientation in FIG. 6C.

Figure 1:
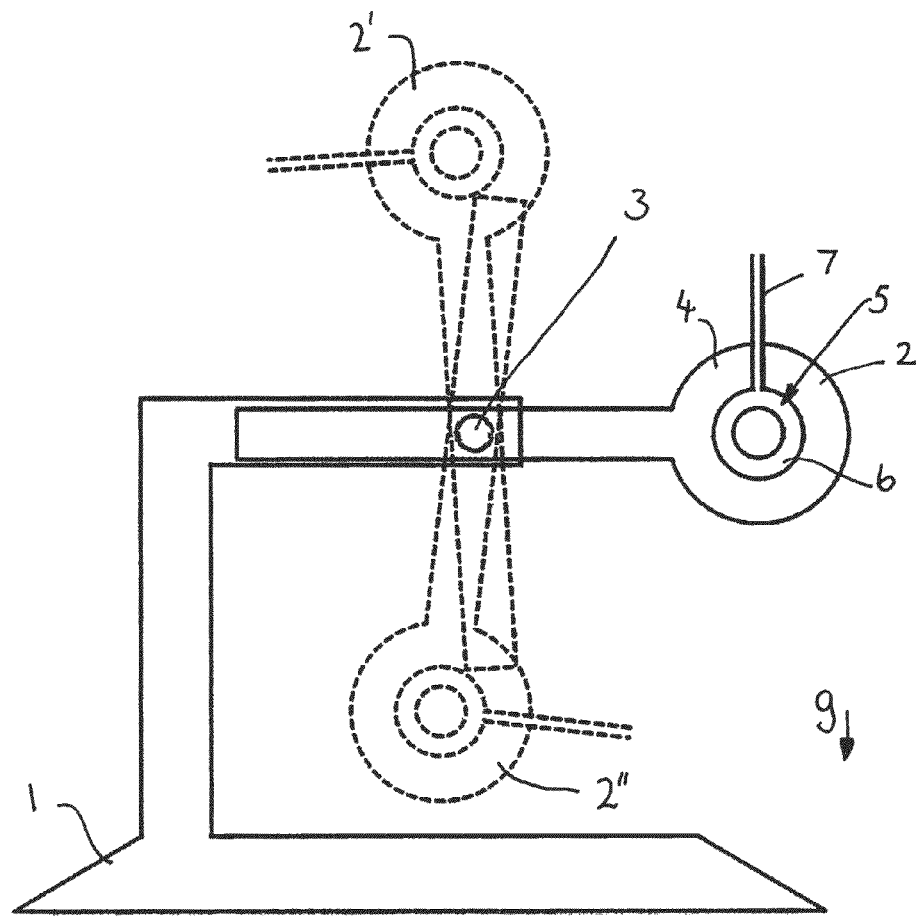

FIG. 1 schematically shows medical equipment apparatus which may, for example, be a gantry mounted cyclotron for use in proton therapy treatment or more generally radiotherapy (radiation therapy) apparatus. The apparatus comprises a base 1 which supports a superconducting magnet arrangement 2 for movement about an axis 3. The superconducting magnet arrangement 2 may be moved between a first position shown in dotted lines and labelled 2' in FIG. 1, and a second position also shown in dotted lines and labelled 2" in FIG. 1 by rotation about the axis 3. It will be appreciated that when the superconducting magnet arrangement 2 is in the first position 2' it has a different orientation relative to the base 1 (as well as relative to the surroundings and in particular relative to gravity) than when the superconducting magnet arrangement is in the second position 2". The superconducting magnet arrangement 2 can be considered to have a first orientation when in the first position 2', and a second orientation when in the second position 2". Further the superconducting magnet arrangement 2 will have a range of intermediate orientations when the superconducting magnet arrangement 2 is between these two positions.

The superconducting magnet arrangement 2 comprises a superconducting magnet 4 and a cryostat 5 for holding cryogenic liquid to maintain the magnet 4 at superconducting temperatures. The cryostat 5 comprises a vessel 6 and quench duct 7. The vessel 6 is for holding the cryogenic liquid, and as mentioned in the introduction, the quench duct 7 is provided for allowing escape of cryogenic fluid and in particular quickly expanding cryogenic gas in the event of the magnet 4 experiencing a quench. The interior of the quench duct 7 is in fluid communication with the vessel 6. The end of the quench duct 7 where it meets the vessel 6 is open. Thus the quench duct will tend to fill with cryogenic gas in normal operation. An alternative arrangement with which the present invention is not concerned is to provide a seal or burst disc at the lower end of the quench duct and evacuate the quench duct. In practice this is difficult and expensive to achieve and the present techniques avoid needing to attempt this.

As is typical, but not shown in the drawings, the cryostat 5 also comprises a fill tube and a vent tube to allow normal filling of the cryostat with cryogenic liquid and normal venting of the vessel 6.

As mentioned above in the introduction, a quench duct 7 typically has a relatively large cross section to allow escape of gas during quenching of the magnet 4. Thus, for example, the quench duct 7 may be a relatively large diameter tube. This is true in the present embodiment.

The outlet end of the tube is capped with a burst disc (not shown in FIG. 1) which is designed to rupture at a set over pressure. Thus, in normal circumstances the burst disc will remain intact and only burst if the quench duct 7 needs to provide its operation of allowing quick evacuation of gas from the vessel 6 which would typically be due to a quench having occurred.

The quench duct 7 is shown only in highly schematic form in FIG. 1 and more details of possible configurations of the quench duct 7 will now be described below with reference to the remaining Figures.

Figure 2:
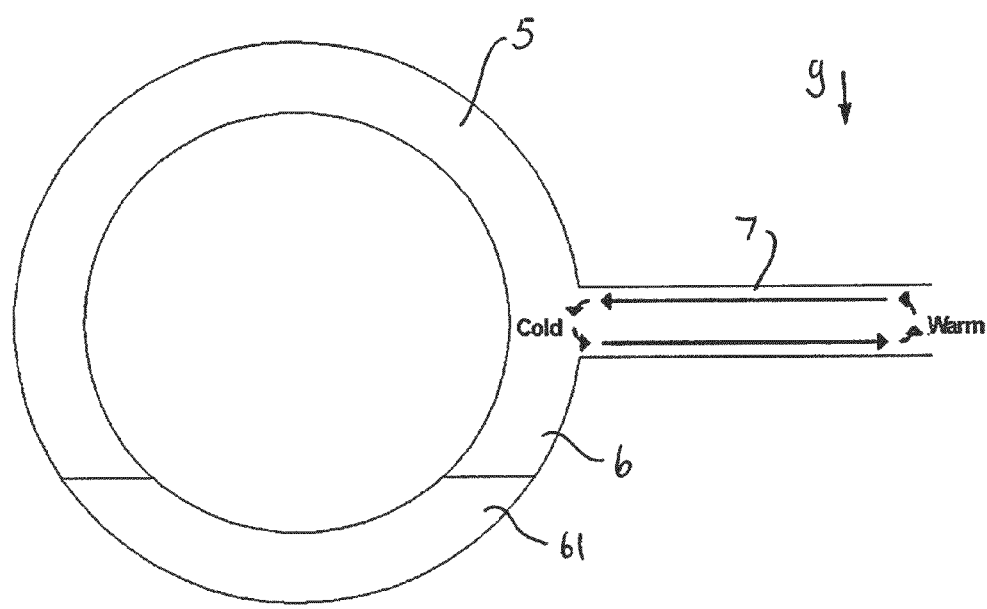
FIG. 2 shows a cryostat of a type which may be used in the apparatus of FIG. 1 and having a conventional quench duct.

FIG. 2 shows a conventional cryostat 5 with a vessel 6 carrying carrying cryogenic liquid 61 and conventional quench duct 7. The quench duct 7 is a straight tube. Where this type of quench duct 7 is used in a static superconducting magnet arrangement no particular problems should occur. The quench duct 7 would be arranged vertically or near vertically providing a temperature inversion in the quench duct such that the quench duct 7 acts as an anti-convection portion. Cryogenic gas boiled off from the cryogenic liquid 61 will fill the quench duct 7 but the gas will remain essentially static due to the temperature inversion.

If such a cryostat 5 is used in an apparatus of the type shown in FIG. 1 then in one or at least some of the orientations described in relation to FIG. 1 the quench duct 7 will behave in the desired way. However in other orientations it will not. Thus, for example, if the cryostat 5 is orientated so that the quench duct 7 is vertical or near vertical when the superconducting magnet arrangement 2 is in the intermediate position as shown in solid lines in FIG. 1, then when the magnet arrangement 2 is moved to either the first position 2' or second position 2" shown in dotted lines then the quench duct 7 will become near horizontal. Such an orientation is shown in FIG. 2 where the direction of gravity g is indicated with an arrow. In this orientation a convection cell is set up which will tend to allow heat to leak into the vessel 6 increasing boil off as discussed in the introduction above.

FIGS. 3A to 3C through to FIGS. 6A to 6C show alternative cryostats 5 which are arranged as multi orientation or rotatable cryostats for alleviating this problem. Each of these cryostats 5 shown in FIGS. 3A to 3C through to FIGS. 6A to 6C are of a type which may be used in the apparatus shown in FIG. 1.

Furthermore in each case, the cryostat 5 is shown in three different orientations. In each case, Figure XA shows the cryostat in an orientation which corresponds to the superconducting magnet arrangement 2 being in the first position 2' shown in FIG. 1, whereas Figure XB shows the cryostat 5 in an orientation which corresponds to the superconducting magnet arrangement 2 being in the second position 2" shown in FIG. 1, and Figure XC shows the cryostat 5 in an orientation which corresponds to the superconducting magnet arrangement 2 being in the intermediate position shown in solid lines in FIG. 1.

In each case in use the vessel 6 holds cryogenic liquid 61, and an inlet end 72 of the quench duct 7 meets with and is open to this vessel 6. On the other hand the other end of the quench duct 7 must proceed to the exterior of the magnet arrangement 2 so as to allow escape of cryogenic gas generated during quenching of the magnet 4 should this occur. This other, outlet, end is capped with a burst disc 73 and in all normal circumstances there will be cryogenic gas present in the quench duct 7. Portions of the quench duct nearer to the vessel 6 will be at a lower temperature than portions away from the vessel 6. Correspondingly the gas nearer the burst disc 73 will be warmer than that nearer the vessel 6.

Turning now to consider the cryostats 5 individually, FIGS. 3A to 3C show a first rotatable cryostat 5 which embodies the invention and is suitable for use in the apparatus of FIG. 1. The cryostat 5 includes a sinuous (or serpentine) quench duct 7 which is arranged to provide anti-convection portions 71 when the cryostat 5 is in the first orientation as shown in FIG. 3A corresponding to the first position 2' of the magnet arrangement 2 in FIG. 1, and when in a second orientation as shown in FIG. 3B corresponding to the magnet arrangement 2 being in the second position 2" shown in FIG. 1, as well as in a third orientation as shown in FIG. 3C corresponding to the magnet arrangement 2 being in the intermediate position shown in solid lines in FIG. 1.

In each case the anti convection portion 71 is a portion of the quench duct 7 in which a temperature inversion will exist in use in a corresponding orientation.

In the present embodiment the quench duct 7 includes a 360 degree loop portion 74 which as seen by reference 3A, 3B and 3C provides an anti-convection portion 71 for use in each of the illustrated operational orientations of the cryostat 5. Further, it will be noted that in intermediate orientations between the orientations shown in FIGS. 3A, 3B and 3C, other portions of the 360 degree loop portion 74 will act as anti-convection portions. An anti-convection portion is provided for each operational orientation of the cryostat 5. In each case, the anti-convection portion is a portion of the quench duct 7 which is upwardly orientated and may be vertical or substantially vertical and which has a lower end 71a which is nearer (in terms of the flow path from the vessel through the quench duct 7) to the vessel 6 than its upper end 71b. This configuration gives rise to the desired temperature inversion in use. Note that each anti-convection portion 71 is a portion of duct tubing. It is open and free of any impediments to fluid flow. This is so it can provide its function as part of the quench duct when required.

The provision of a loop portion, for example the 360 degree loop portion 74 in the quench duct 7, is desirable because it means that as the cryostat 6 moves from the first orientation shown in FIG. 3A to the second orientation shown in FIG. 3B through the intermediate orientation shown in FIG. 3C the effective anti-convection portion 71 moves smoothly around the loop portion 74. This helps to provide a more continuous anti-convection effect than if the effective anti-convection portion jumps from location to location since in such a case there will be more of time required in order for the flow to stabilise as the temperature inversion takes effect in any given orientation.

The cryostat shown in FIGS. 3A to 3C provides good operation in orientations of plus or minus 110 degrees from a central position as shown in FIG. 3C.

FIGS. 4A to 4C show a similar cryostat 5 to that shown in FIGS. 3A to 3C. However here the loop portion 74 is replaced by a spiral portion 75. Again anti-convection portions 71 are provided by the quench duct 7 for each of the three different orientations shown. Further, different anti-convection portions exist for intermediate orientations between those shown in FIGS. 4A to 4C. It will be noted that in the embodiment of FIGS. 3A to 3C the loop portion 74 is provided close to parallel to a plane which has the axis of rotation 3 as normal. On the other hand, the spiral bend portion 75 of the FIG. 4A to 4C arrangement is approximately perpendicular to this plane.

Figure 5B:
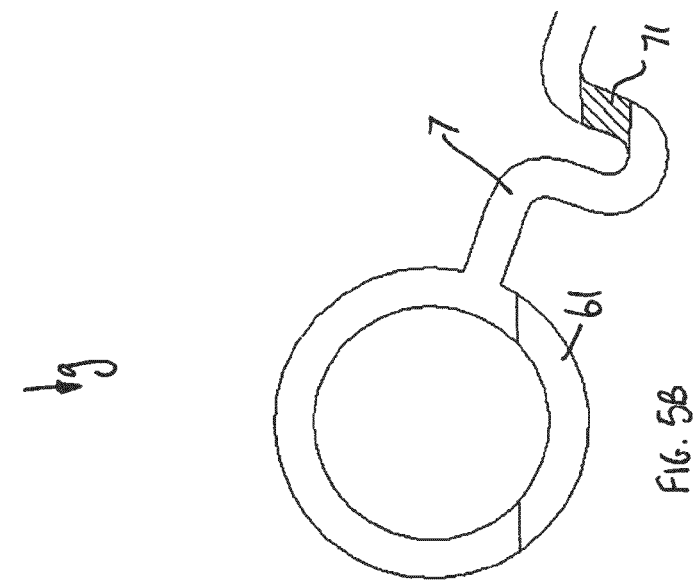
FIGS. 5A to 5C show a third rotatable cryostat embodying the invention which may be used in the apparatus shown in FIG. 1, with the cryostat shown in a first orientation in FIG. 5A, a second orientation in FIG. 5B, and an intermediate orientation in FIG. 5C.
Figure 5C:
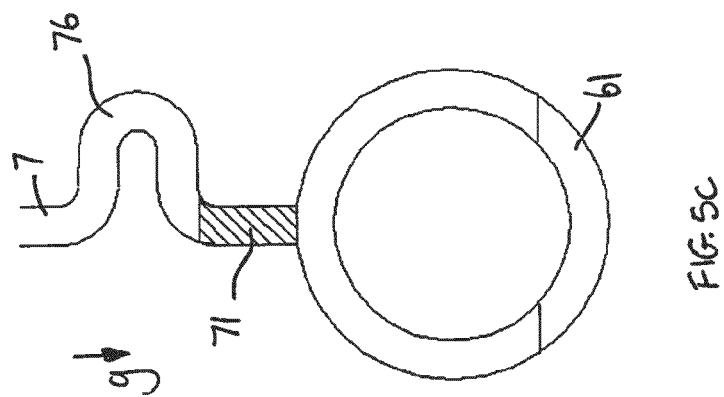
Figure 5A:
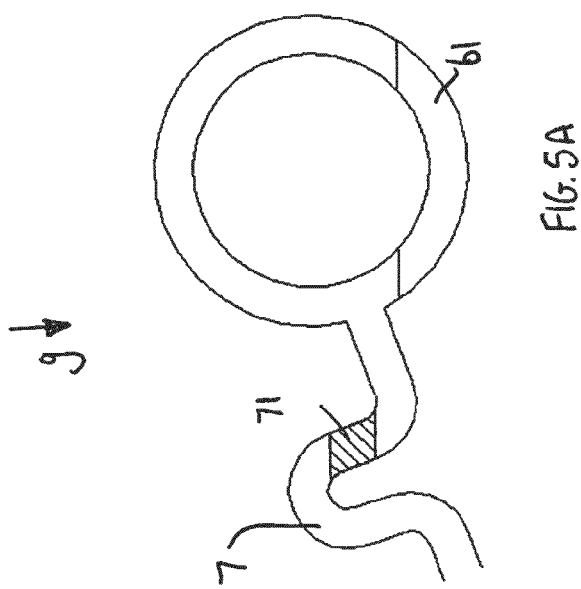

FIGS. 5A to 5C show a third cryostat 5 embodying the present invention. In this case the quench duct 7 includes a U-bend portion 76 in place of the loop portion 74 of the quench duct of FIGS. 3A to 3C. Again, this U-bend 76 is provided largely in a plane which has as a normal axis of rotation 2. The quench duct 7 again provides anti-convection portions 71 which are operative in the different orientations of the cryostat 5 shown in FIGS. 5A, 5B and 5C. Again anti-convection portions exist for orientations between these orientations.

It may be noted that in each of the embodiments shown in FIGS. 3A to 3C, 4A to 4C and 5A to 5C the inlet portion 72 of the quench duct 7 acts as an anti-convection portion for at least one orientation. This is desirable and may indeed be typical but is not essential.

FIGS. 6A to 6C show a fourth cryostat 5 embodying the present invention. Again there is a vessel 6 (shown only highly schematically and in dotted lines in the drawings) and leading away from this a quench duct 7. However, here the quench duct 7 is even more convoluted or more sinuous than in the embodiments described above. This quench duct 7 includes multiple turns 77 and straight sections 78 therebetween. In the present embodiment each turn 77 is in the form of a U-bend. Again the quench duct 7 is provided primarily in a plane which has as a normal the axis of rotation 2. Here again an anti-convection portion 71 is provided for each of the orientations shown in FIGS. 6A, 6B and 6C and anti-convection portions also exist for intermediate orientations. In the present embodiment in fact there may be a plurality of anti-convection portions 71 which are operative in any one orientation.

It should be noted that whilst having the anti-convection portion 71 in any one of these embodiments completely vertical is ideal, this is not essential. Provided that the portion is angled upwardly at least some effect will be achieved and this will improve as this becomes close to vertical.

Note that the direction of gravity relative to the cryostat 5 is shown with an arrow labelled g in each of the Figures. This corresponds to the section labelled as an anti-convection portion 71 in the respective drawing.

Note that the quench duct 7 in each case is made of a relatively large diameter tube and it is desirable for each anti-convection portion to be as long as possible relative to the diameter of the tube. In some cases, however, at least reasonable performance may be achieved if the length of the anti-convection portion is at least equal to or exceeds the diameter of the tube.

Note also that the inlet portion 72 of the quench duct 7 is located towards an upper portion of the vessel 6 when the cryostat 5 is in an orientation which is midway between its operational extremes, i.e. equivalent to the position shown in Figures XC above. This can help ensure that the quench duct remains free of liquid in all operational orientations.

Outside of the magnet 4 itself, the quench duct 7 may have a diameter in the order of 100 mm. Inside the magnet arrangement 5 itself the quench duct may have a smaller diameter. Ideally this is for a relatively short length of the quench duct.

It may be noted that the quench duct 7 shown in FIGS. 6A to 6D would provide a relatively high flow resistance compared with arrangements shown in FIGS. 3A to 3C to FIGS. 5A to 5C.

The exact configuration of the quench duct 7 which will be acceptable in a particular superconducting magnet arrangement depends on the construction of that arrangement as a whole. Thus an arrangement such as that shown in FIGS. 6A to 6C may only be suitable where the cryostat 5 is for holding a relatively small volume of cryogenic liquid and the potential rate of boil off due to a quench of the magnet is relatively low.

Note that a typical vent outlet for handling normal boil of rather than boil off created by a quench will normally be provided with a non return valve which will not in general allow a fast enough exit of gas to cope with a quench.

Note that whilst the above relates to cryostats which may be used in different orientations which are reachable from one another by a rotational transformation and hence the cryostat may be described as a rotatable cryostat this does not imply that the cryostat must be rotatable though 360 degrees or continuously rotatable nor indeed that it should necessarily be or is mounted for rotation. Rather we are defining how the orientations are related to one another.

The invention claimed is:

1. A multi-orientation cryostat for a superconducting magnet for use in a plurality of orientations, the cryostat comprising a vessel for holding cryogenic liquid and, leading away from the vessel, a quench duct for allowing escape from the vessel of gas generated by boiling of the cryogenic liquid due to quenching of the magnet, wherein the quench duct is sinuous so as to provide at least two differently orientated anti-convection portions, each portion for functioning as an anti-convection portion with the cryostat in a respective corresponding orientation, wherein the quench duct does not wrap around the cryostat vessel.

2. A multi-orientation cryostat according to claim 1 in which the quench duct comprises more than two anti-convection portions.

3. A multi-orientation cryostat according to claim 1 in which the orientation of at least one of the anti-convection portions is separated by at least 90 degrees from the orientation of at least another one of the anti-convection portions.

4. A multi-orientation cryostat according to claim 1 in which the quench duct has an inlet portion which is arranged to remain above the level of the carried cryogenic liquid in normal operation.

5. A multi-orientation cryostat according to claim 1 in which the multi-orientation cryostat is arranged for use in a first orientation and a second orientation reachable from the first orientation by a rotational transformation, and arranged for use in orientations between the first orientation and the second orientation reachable by execution of part of said rotational transformation from the first orientation.

6. A multi-orientation cryostat according to claim 5 in which a first portion of the quench duct is for acting as an anti-convection portion when the cryostat is in the first orientation and a second portion of the quench duct is for acting as an anti-convection portion when the cryostat is in the second orientation.

7. A multi-orientation cryostat according to claim 1 in which the quench duct includes a continuous bend portions, such as a u-bend portion, or a loop portion, or a spiral bend portion.

8. A multi-orientation cryostat according to claim 7 in which the continuous bend portion turns through at least 90 degrees, preferably in the order of at least 180 degrees.

9. A multi-orientation cryostat according to claim 1 in which the cryostat comprises a single quench duct.

10. A superconducting magnet arrangement comprising a superconducting magnet and multi-orientation cryostat for use in a plurality of orientations, the cryostat comprising a vessel for holding cryogenic liquid and, leading away from the vessel, a quench duct for allowing escape from the vessel of gas generated by boiling of the cryogenic liquid due to quenching of the magnet, wherein the quench duct is sinuous so as to provide at least two differently orientated anti-convection portions, each portion for functioning as an anti-convection portion with the cryostat in a respective corresponding orientation, wherein the quench duct the quench duct does not wrap around the cryostat vessel.

11. Medical equipment apparatus comprising a superconducting magnet arrangement comprising a superconducting magnet and multi-orientation cryostat for use in a plurality of orientations, the cryostat comprising a vessel for holding cryogenic liquid and, leading away from the vessel, a quench duct for allowing escape from the vessel of gas generated by boiling of the cryogenic liquid due to quenching of the magnet, wherein the quench duct is sinuous so as to provide at least two differently orientated anti-convection portions, each portion for functioning as an anti-convection portion with the cryostat in a respective corresponding orientation, which superconducting magnet arrangement is mounted for movement relative to a base of the medical equipment apparatus between a first position where the cryostat is in a first orientation and a second position where the cryostat is in a second orientation, wherein the quench duct does not wrap around the cryostat vessel.

12. Medical equipment apparatus comprising a superconducting magnet arrangement mounted for movement relative to a base of the medical equipment apparatus between a first position and a second position,
the superconducting magnet arrangement comprising a superconducting magnet and a cryostat comprising a vessel for holding cryogenic liquid and, leading away from the vessel, a quench duct for allowing escape from the vessel of gas generated by boiling of the cryogenic liquid due to quenching of the magnet, wherein the cryostat is in a first orientation when the magnet arrangement is in the first position and the cryostat is in a second orientation when the magnet arrangement is in the second position and wherein, the quench duct is sinuous so as to provide at least a first portion and a second portion which are differently orientated from one another in such a way that:
when the cryostat is in the first orientation, the first portion extends upwardly relative to the base of the equipment and has a lower end and an upper end with the lower end closer, in terms of a flow path through the quench duct from the vessel, to the vessel than the upper end; and
when the cryostat is in the second orientation, the second portion extends upwardly relative to the base of the equipment and has a lower end and an upper end with the lower end closer, in terms of a flow path through the quench duct from the vessel, to the vessel than the upper end, wherein the quench duct does not wrap around the cryostat vessel.

13. A multi-orientation cryostat according to claim 1 in which a burst disc is provided, one of at an end of, and towards an end of, the quench duct remote from the vessel.

14. A multi-orientation cryostat according to claim 1 in which the quench duct is arranged to extend outside of the magnet, and a portion of the quench duct extending outside of the magnet has a larger diameter than a portion inside of the magnet.

15. A multi-orientation cryostat for a superconducting magnet for use in a plurality of orientations, the cryostat comprising a vessel for holding cryogenic liquid and, leading away from the vessel, a quench duct for allowing escape from the vessel of gas generated by boiling of the cryogenic liquid due to quenching of the magnet, wherein the quench duct is sinuous so as to provide at least two differently orientated anti-convection portions, each portion for functioning as an anti-convection portion with the cryostat in a respective corresponding orientation, wherein a burst disc is provided one of, at an end of and towards an end of, the quench duct remote from the vessel.

16. A multi-orientation cryostat for a superconducting magnet for use in a plurality of orientations, the cryostat comprising a vessel holding cryogenic liquid and, leading away from the vessel, a quench duct for allowing escape from the vessel of gas generated by boiling of the cryogenic liquid due to quenching of the magnet, wherein the quench duct is sinuous so as to provide at least two differently orientated anti-convection portions, each portion for functioning as an anti-convection portion with the cryostat in a respective corresponding orientation,
wherein the multi-orientation cryostat is arranged for use in a first orientation and a second orientation reachable from the first orientation by a rotational transformation, and arranged for use in orientations between the first orientation and the second orientation reachable by execution of part of said rotational transformation from the first orientation, there being at least 135 degrees of rotation between the first orientation and the second orientation, and
wherein the quench duct has an inlet portion which remains above the level of the cryogenic liquid held in the vessel in normal operation, comprising when the cryostat is in the first orientation, the second orientation and orientations between the first and second orientations.

17. A multi-orientation cryostat according to claim 16 in which a first portion of the quench duct is for acting as an anti-convection portion when the cryostat is in the first orientation and a second portion of the quench duct is for acting as an anti-convection portion when the cryostat is in the second orientation.

18. A multi-orientation cryostat according to claim 16 in which the cryostat comprises a single quench duct.

19. A multi-orientation cryostat according to claim 16 in which the quench duct includes a continuous bend portions, such as a u-bend portion, or a loop portion, or a spiral bend portion.

20. A multi-orientation cryostat according to claim 19 in which the continuous bend portion turns through at least 90 degrees, preferably in the order of at least 180 degrees.

21. A superconducting magnet arrangement comprising a superconducting magnet and multi-orientation cryostat for use in a plurality of orientations, the cryostat comprising a vessel holding cryogenic liquid and, leading away from the vessel, a quench duct for allowing escape from the vessel of gas generated by boiling of the cryogenic liquid due to quenching of the magnet, wherein the quench duct is sinuous so as to provide at least two differently orientated anti-convection portions, each portion for functioning as an anti-convection portion with the cryostat in a respective corresponding orientation,
wherein the multi-orientation cryostat is arranged for use in a first orientation and a second orientation reachable from the first orientation by a rotational transformation, and arranged for use in orientations between the first orientation and the second orientation reachable by execution of part of said rotational transformation from the first orientation, there being at least 135 degrees of rotation between the first orientation and the second orientation, and
wherein the quench duct has an inlet portion which remains above the level of the cryogenic liquid held in the vessel in normal operation, comprising when the cryostat is in the first orientation, the second orientation and orientations between the first and second orientations.

22. Medical equipment apparatus comprising a superconducting magnet arrangement comprising a superconducting magnet and multi-orientation cryostat for use in a plurality of orientations, the cryostat comprising a vessel holding cryogenic liquid and, leading away from the vessel, a quench duct for allowing escape from the vessel of gas generated by boiling of the cryogenic liquid due to quenching of the magnet, wherein the quench duct is sinuous so as to provide at least two differently orientated anti-convection portions, each portion for functioning as an anti-convection portion with the cryostat in a respective corresponding orientation, wherein the multi-orientation cryostat is arranged for use in a first orientation and a second orientation reachable from the first orientation by a rotational transformation, and arranged for use in orientations between the first orientation and the second orientation reachable by execution of part of said rotational transformation from the first orientation, there being at least 135 degrees of rotation between the first orientation and the second orientation, and wherein the quench duct has an inlet portion which remains above the level of the cryogenic liquid held in the vessel in normal operation, comprising when the cryostat is in the first orientation, the second orientation and orientations between the first and second orientations, and wherein the superconducting magnet arrangement is mounted for movement relative to a base of the medical equipment apparatus between a first position where the cryostat is in the first orientation and a second position where the cryostat is in the second orientation.

\* \* \* \* \*

UNITED STATES PATENT AND TRADEMARK OFFICE
CERTIFICATE OF CORRECTION

Page 1 of 1

PATENT NO. : 8,812,067 B2
APPLICATION NO. : 13/428236
DATED : August 19, 2014
INVENTOR(S) : Benjamin David Leigh et al.

It is certified that error appears in the above-identified patent and that said Letters Patent is hereby corrected as shown below:

In the Claims

Column 10, Line 65-66, Claim 10, change

"wherein the quench duct the quench duct does not wrap around the cryostat vessel"

to—

"wherein the quench duct does not wrap around the cryostat vessel"

Signed and Sealed this
Twenty-ninth Day of September, 2015

Michelle K. Lee
*Director of the United States Patent and Trademark Office*